United States Patent
Kim et al.

(10) Patent No.: US 11,198,768 B2
(45) Date of Patent: Dec. 14, 2021

(54) PREPARATION METHOD OF SUPER ABSORBENT POLYMER

(71) Applicant: LG Chem, Ltd., Seoul (KR)

(72) Inventors: Ju Eun Kim, Daejeon (KR); Gi Cheul Kim, Daejeon (KR); Se Yeol Park, Daejeon (KR); Ki Hyun Kim, Daejeon (KR)

(73) Assignee: LG Chem, Ltd.

( * ) Notice: Subject to any disclaimer, the term of this patent is extended or adjusted under 35 U.S.C. 154(b) by 327 days.

(21) Appl. No.: 15/755,325

(22) PCT Filed: Mar. 17, 2016

(86) PCT No.: PCT/KR2016/002725
§ 371 (c)(1),
(2) Date: Feb. 26, 2018

(87) PCT Pub. No.: WO2017/111205
PCT Pub. Date: Jun. 29, 2017

(65) Prior Publication Data
US 2018/0244867 A1    Aug. 30, 2018

(30) Foreign Application Priority Data
Mar. 11, 2016  (KR) .................. 10-2016-0029847

(51) Int. Cl.
| | | |
|---|---|---|
| C08F 2/46 | (2006.01) | |
| C08F 2/50 | (2006.01) | |
| C08G 61/04 | (2006.01) | |
| C08J 3/24 | (2006.01) | |
| C08F 20/06 | (2006.01) | |
| C08J 3/075 | (2006.01) | |
| A61L 15/60 | (2006.01) | |
| C08K 7/22 | (2006.01) | |
| C08K 3/34 | (2006.01) | |
| C08F 2/10 | (2006.01) | |
| C08K 3/36 | (2006.01) | |

(52) U.S. Cl.
CPC .............. *C08J 3/24* (2013.01); *A61L 15/60* (2013.01); *C08F 2/10* (2013.01); *C08F 2/50* (2013.01); *C08F 20/06* (2013.01); *C08J 3/075* (2013.01); *C08J 3/245* (2013.01); *C08K 3/346* (2013.01); *C08K 3/36* (2013.01); *C08K 7/22* (2013.01); *C08J 2333/02* (2013.01)

(58) Field of Classification Search
CPC . C08J 3/24; C08J 3/075; C08J 2333/02; C08J 3/245; C08K 3/36; C08K 3/34; C08F 20/06; C08F 2/10
USPC ................ 522/64, 6, 184, 71, 189, 1; 520/1
See application file for complete search history.

(56) References Cited

U.S. PATENT DOCUMENTS

| | | | |
|---|---|---|---|
| 4,446,261 A | 5/1984 | Yamasaki et al. | |
| 4,587,308 A | 5/1986 | Makita et al. | |
| 4,666,983 A | 5/1987 | Tsubakimoto et al. | |
| 5,475,062 A | 12/1995 | Ishizaki et al. | |
| 7,833,624 B2 | 11/2010 | Harren et al. | |
| 2002/0002226 A1 | 1/2002 | Barnett | |
| 2008/0125533 A1 | 5/2008 | Riegel et al. | |
| 2014/0031473 A1 | 1/2014 | Nogi et al. | |
| 2014/0042364 A1* | 2/2014 | Nogi ................. | C08J 3/245 252/194 |
| 2014/0058048 A1 | 2/2014 | Won et al. | |
| 2015/0087742 A1 | 3/2015 | Won et al. | |
| 2016/0280866 A1 | 9/2016 | Lee et al. | |
| 2016/0311985 A1* | 10/2016 | Jung ................. | A61L 15/60 |

FOREIGN PATENT DOCUMENTS

| | | | | |
|---|---|---|---|---|
| EP | 1105168 | B1 | 7/2002 | |
| EP | 2669319 | A1 | 12/2013 | |
| JP | S56161408 | A | 12/1981 | |
| JP | S57158209 | A | 9/1982 | |
| JP | S57198714 | A | 12/1982 | |
| JP | H04025062 | B2 | 4/1992 | |
| JP | 3068840 | B2 | 7/2000 | |
| JP | 3414778 | B2 | 6/2003 | |
| JP | 2008517116 | A | 5/2008 | |
| KR | 1019950006118 | B1 | 6/1995 | |
| KR | 20110049072 | A | 5/2011 | |
| KR | 20110136597 | A | 12/2011 | |
| KR | 20120054836 | A | 5/2012 | |
| KR | 20130120300 | A | 11/2013 | |
| KR | 20140126280 | A | 10/2014 | |
| KR | 20140133470 | A | 11/2014 | |
| WO | WO-2015088200 | A1 * | 6/2015 | ........... C08F 220/06 |

OTHER PUBLICATIONS

International Search Report fo PCT/KR2016/002725 dated Aug. 24, 2016.
Schwalm, Reinhold, "UV Coatings: Basics, Recent Developments and New Applications", Elsevier Science (Dec. 21, 2006), p. 115.
Odian, George, "Principles of Polymerization", John Wiley and Sons, Inc. 1981, p. 203.
Third Party Observation for Application No. PCT/KR2016/002725 dated Apr. 20, 2018.

* cited by examiner

Primary Examiner — Jessica Whiteley
(74) Attorney, Agent, or Firm — Lerner, David, Littenberg, Krumholz & Mentlik, LLP

(57) ABSTRACT

The present invention relates to a method for preparing superabsorbent polymer. According to the preparation method of the present invention, the surface penetration depth of a surface crosslinking agent can be appropriately controlled, and superabsorbent polymer with excellent properties can be prepared though homogeneous surface crosslinking. Thus, superabsorbent polymer with improved absorption property can be provided without deterioration of absorbency under load.

14 Claims, No Drawings

PREPARATION METHOD OF SUPER ABSORBENT POLYMER

CROSS-REFERENCE TO RELATED APPLICATION

The present application is a national phase entry under 35 U.S.C. § 371 of International Application No. PCT/KR2016/002725, filed on Mar. 17, 2016, which claims the benefit of Korean Patent Application No. 10-2015-0184917 filed on Dec. 23, 2015 and Korean Patent Application No. 10-2016-0029847, filed on Mar. 11, 2016 with the Korean Intellectual Property Office, the disclosures of which are herein incorporated by reference.

BACKGROUND OF THE INVENTION

(a) Field of the Invention

The present invention relates to a method for preparing superabsorbent polymer. More specifically, the present invention relates to a method for preparing superabsorbent polymer with improved absorption property without deterioration of centrifuge retention capacity and absorbency under load.

(b) Description of the Related Art

Super absorbent polymer (SAP) is synthetic polymer material that can absorb moisture of 500 to 1000 times of self-weight, and is also named differently as super absorbency material (SAM), absorbent gel material (AGM), etc. according to developing companies. The superabsorbent polymer began to be commercialized as sanitary items, and currently, it is being widely used as hygienic goods such as a disposable diaper and so on, water-holding material for soil, water stop material for civil engineering and architecture, sheets for raising seedling, freshness preservatives in the field of food circulation, fomentation material, etc.

As a method for preparing the superabsorbent polymer, reverse phase suspension polymerization or water-soluble solution polymerization, etc. are known. The reverse phase suspension polymerization is disclosed, for example, in Japanese Laid-Open Patent Publication No. Sho 56-161408, Japanese Laid-Open Patent Publication No. Sho 57-158209, and Japanese Laid-Open Patent Publication No. Sho 57-198714, etc. As the water-soluble solution polymerization, thermal polymerization wherein hydrogel polymer is polymerized while being fractured and cooled in a kneader equipped with many axes, and photopolymerization wherein a water-soluble solution of high concentration is irradiated by UV, etc. on a belt, thus simultaneously conducting polymerization and drying, are known.

Meanwhile, hydrogel polymer obtained through the polymerization is generally passed through a drying process and ground, and then, passed through a step of selectively crosslinking the polymer surface so as to have desired absorption capacity and absorbency under load. In the surface crosslinking, it is required to control the penetration depth of the surface crosslinking agent, and for this, in general, the penetration depth of the surface crosslinking agent was controlled using alcohol and water. However, in case the penetration depth is controlled using alcohol, a large quantity of alcohol is consumed, which is unfavorable in terms of cost, and additional drying treatment is required.

Therefore, in order to overcome the problems, methods of minimizing the amount of alcohol used or methods without using alcohol have been suggested. However, if the amount of alcohol used is excessively reduced, water may be excessively absorbed in the polymer, thus rendering efficient crosslinking difficult due to the agglomeration of gel.

SUMMARY OF THE INVENTION

It is an object of the present invention to provide a method for preparing superabsorbent polymer that conducts surface crosslinking using a surface crosslinking agent fulfilling specific conditions, thereby controlling the penetration depth of the surface crosslinking agent, and thus, can further improve the properties of the final product, and particularly, can improve absorption property without deterioration of absorbency under load.

In order to solve the object, one aspect of the present invention provides a method for preparing superabsorbent polymer comprising the steps of:

performing thermal polymerization or photopolymerization of a monomer composition comprising water-soluble ethylenically unsaturated monomers and a polymerization initiator to form hydrogel polymer;

drying the hydrogel polymer;

grinding the dried polymer; and mixing the ground polymer with a surface crosslinking agent comprising hydrophobic alcohol to conduct a surface crosslinking reaction.

The preparation method of superabsorbent polymer according to the present invention uses hydrophobic alcohol having a carbon number of 4 or more as a surface crosslinking agent instead of hydrophilic alcohol previously commonly used, and thus, can appropriately control the surface penetration depth of the surface crosslinking agent, and can prepare superabsorbent polymer with excellent properties through homogeneous surface crosslinking.

Thereby, the properties of the product can be further improved, and particularly, superabsorbent polymer with improved absorption property without deterioration of absorbency under load can be provided.

DETAILED DESCRIPTION OF THE EMBODIMENTS

Technical terms in the present specification are only for mentioning specific embodiments, and they are not intended to restrict the present invention unless there is a particular mention about them. The singular expressions used herein may include the plural expressions unless they are differently expressed contextually. The meaning of the term "include" used in the specification embodies specific characteristics, areas, essences, steps, actions, elements, and/or components, and does not exclude existence or addition of other specific characteristics, areas, essences, steps, actions, elements, components, and/or groups.

Although various modifications can be made to the present invention and the present invention may have various forms, specific examples will be illustrated and explained in detail below. However, it should be understood that these are not intended to limit the present invention to specific disclosure, and that the present invention includes all the modifications, equivalents or replacements thereof without departing from the spirit and technical scope of the invention.

Hereinafter, a method for preparing superabsorbent polymer according to specific embodiment of the present invention will be explained in more detail.

The preparation method of superabsorbent polymer comprises the steps of: progressing thermal polymerization or photopolymerization of a monomer composition comprising water-soluble ethylenically unsaturated monomers and a polymerization initiator to form hydrogel polymer; drying the hydrogel polymer; grinding the dried polymer; and mixing the ground polymer with a surface crosslinking agent comprising hydrophobic alcohol to conduct a surface crosslinking reaction.

For reference, as used herein, "polymer" means the polymerized state of water-soluble ethylenically unsaturated monomers, and may include those of all moisture content ranges or particle diameter ranges. Among the polymers, those having moisture content of about 40 wt % or more after polymerized and before dried may be designated as hydrogel polymer.

And, "base resin" or "base resin powder" means the powder form of polymer made by drying and grinding.

And, "superabsorbent polymer" means the polymer or base resin itself according to the context, or it is used to include those made to be appropriate for productization through additional processes, for example, surface crosslinking, particle reassembly, drying, grinding, sieving, etc. of the polymer or base resin.

In the preparation method of the present invention according to the above explained embodiment, the steps of forming hydrogel polymer, drying the hydrogel polymer, and grinding the dried polymer may be conducted by steps and methods commonly used in the technical field for the preparation of superabsorbent polymer.

First, specifically, the monomer composition, which is raw material of the superabsorbent polymer, comprises water-soluble ethylenically unsaturated monomers and a polymerization initiator.

As the water-soluble ethylenically unsaturated monomers, monomers commonly used in the preparation of superabsorbent polymer may be used without limitation in the constructions. Largely, one or more selected from the group consisting of anionic monomers and salts thereof, non-ionic hydrophilic containing monomers, and amino group containing unsaturated monomers and quaternarized products thereof may be used.

Specifically, as the water-soluble ethylenically unsaturated monomers, one or more selected from the group consisting of anionic monomers and salts thereof such as acrylic acid, methacrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid or 2-(meth)acrylamide-2-methyl propane sulfonic acid; non-ionic hydrophilic group containing monomers such as (meth)acrylamide, N-substituted (meth)acrylate, 2-hydroxyethyl (meth)acrylate, 2-hydroxypropyl (meth)acrylate, methoxy polyethylene glycol (meth)acrylate, or polyethylene glycol (meth)acrylate; and amino group containing unsaturated monomers such as (N,N)-dimethylaminoethyl (meth)acrylate, (N,N)-dimethylaminopropyl (meth)acrylamide, and quaternarized products thereof, may be preferably used.

More preferably, acrylic acid or salts thereof, for example, acrylic acid and/or alkali metal salts such as a sodium salt thereof may be used, and by using such monomers, superabsorbent polymer having more excellent properties can be prepared. In case the alkali metal salt of acrylic acid is used as monomers, the acrylic acid may be neutralized with a basic compound such as caustic soda (NaOH) before use. Here, the degree of neutralization of the water-soluble ethylenically unsaturated monomers may be controlled to about 50 to 95% or about 70 to 85%, within which superabsorbent polymer having excellent centrifuge retention capacity can be provided without concern for precipitation during neutralization.

The concentration of the water-soluble ethylenically unsaturated monomers may be controlled to about 20 to about 60 wt %, or about 40 to about 50 wt %, based on the monomer composition comprising raw materials of the superabsorbent polymer and a solvent, and may be appropriately controlled considering polymerization time and reaction conditions, etc. However, if the concentration of the monomers becomes too low, yield of superabsorbent polymer may decrease, thus causing economical problems, and if the concentration becomes too high, process problems may be generated such as precipitation of a part of the monomers or low grinding efficiency during grinding of polymerized hydrogel polymer, etc., and the properties of superabsorbent polymer may be deteriorated.

The polymerization initiator used in the preparation method of superabsorbent polymer of the present invention is not specifically limited as long as it is commonly used for the preparation of superabsorbent polymer.

Specifically, as the polymerization initiators, a thermal polymerization initiator or a photopolymerization initiator according to UV irradiation may be used according to polymerization methods. However, even in the case of photopolymerization, since a certain amount of heat is generated by UV irradiation, etc., and heat is generated to some degree according to the progression of an exothermic polymerization reaction, a thermal polymerization initiator may be additionally included.

The photopolymerization initiator is not limited in terms of its construction, as long as it is a compound capable of forming a radical by light such as UV.

Specifically, as the thermal polymerization initiator, at least one selected from the group consisting of a persulfate initiator, an azo initiator, hydrogen peroxide, and ascorbic acid may be used. Specific examples of the persulfate initiator may include sodium persulfate ($Na_2S_2O_8$), potassium persulfate ($K_2S_2O_8$), ammonium persulfate (($NH_4$)$_2S_2O_8$), etc., and, specific examples of the azo initiator may include 2,2-azobis(2-amidinopropane)dihydrochloride, 2,2-azobis-(N,N-dimethylene)isobutyramidinedihydrochloride, 2-(carbamoylazo)isobutyronitril, 2,2-azobis[2-(2-imidazolin-2-yl)propane]dihydrochloride, 4,4-azobis-(4-cyanovalericacid), etc. More various thermal initiators are described in "Principle of Polymerization (Wiley, 1981)", Odian, page 203, and are not limited to the above described examples.

The thermal polymerization initiator may be included in the concentration of about 0.001 to about 0.5 wt %, based on the monomer composition. If the concentration of the thermal polymerization initiator is too low, additional thermal polymerization may hardly occur, and thus, the effect obtained by the addition of the thermal polymerization initiator may be insignificant, and if the concentration of the thermal polymerization initiator is too high, the molecular weight of the superabsorbent polymer may become small, and the properties may become non-uniform.

As the photopolymerization initiator, one or more selected from the group consisting of benzoin ether, dialkyl acetophenone, hydroxyl alkylketone, phenyl glyoxylate, benzyl dimethyl ketal, acyl phosphine, and α-aminoketone may be used. As the specific example of the acyl phosphine, commercially used lucirin TPO, namely, 2,4,6-trimethyl-benzoyl-trimethyl phosphine oxide may be used. More various photopolymerization initiators are described in Reinhold Schwalm, "UV Coatings: Basics, Recent Developments and New Application (Elsevier 2007)", page 115, and are not limited to the above described examples.

The photopolymerization initiator may be added in the concentration of about 0.005 to about 1.0 wt %, based on the monomer composition. If the concentration of the photopolymerization initiator is too low, polymerization speed may become slow, and if the concentration of the polymerization initiator is too high, the molecular weight of the superabsorbent polymer may become small and the properties may become nonuniform.

According to one embodiment of the present invention, the monomer composition may further comprise an internal crosslinking agent as the raw material of superabsorbent polymer. As the internal crosslinking agent, a crosslinking agent that has one or more functional groups capable of reacting with the water-soluble substituent of the water-soluble ethylenically unsaturated monomers, and has one or more ethylenically unsaturated groups; or a crosslinking agent that has two or more functional groups capable of reacting with the water-soluble substituent of the monomers and/or water-soluble substituent formed by the hydrolysis of the monomers may be used.

Specific examples of the internal crosslinking agent may include C8-C12 bisacrylamide, bismetharylamide, poly (meth)acrylate of C2-C10 polyol or poly(meth)allylether of C2-C10 polyol, etc., and more specifically, one or more selected from the group consisting of N,N'-methylenebis (meth)acrylate, ethyleneoxy(meth)acrylate, polyethyleneoxy(meth)acrylate, propyleneoxy(meth)acrylate, glycerin diacrylate, glycerin triacrylate, trimethylol triacrylate, triallylamine, triarylcyanurate, triallylisocyanate, polyethyleneglycol, diethyleneglycol and propyleneglycol may be used.

The internal cross linking agent may be included in the concentration of about 0.001 to about 2.0 wt %, based on the monomer mixture, thus cross linking the polymerized polymer.

In the preparation method of the preset invention, the monomer composition of superabsorbent polymer may further comprise additives such as a thickener, a plasticizer, a preservation stabilizer, an antioxidant, etc., as necessary.

The above explained raw materials such as water-soluble ethylenically unsaturated monomers, photopolymerization initiator, thermal polymerization initiator, internal cross linking agent and additives may be provided in the form of a monomer composition solution dissolved in a solvent.

Here, the solvent that can be used is not limited in terms of its construction as long as it can dissolve the above explained components, and for example, one or more selected from water, ethanol, ethyleneglycol, diethyleneglycol, triethyleneglycol, 1,4-butanediol, propyleneglycol, ethyleneglycol monobutyl ether, propyleneglycol monomethyl ether, propyleneglycol monomethyl ether acetate, methylethylketone, acetone, methylamylketone, cyclohexanone, cyclopentanone, diethyleneglycol monomethyl ether, diethyleneglycol ethyl ether, toluene, xylene, butyrolactone, carbitol, methylcellosolve acetate and N,N-dimethylacetamide, etc. may be used alone or in combination.

The solvent may be included in the remaining amount excluding the above-explained components, based on the total amount of the monomer composition.

Meanwhile, a method of forming hydrogel polymer by the thermal polymerization or photopolymerization of the monomer composition is not specifically limited in terms of its construction, as long as it is a commonly used polymerization method. Specifically, the polymerization method is largely classified into thermal polymerization and photopolymerization according to energy source, and commonly, thermal polymerization may be progressed in a reactor equipped with a stirring axis such as a kneader, and photopolymerization may be progressed in a reactor equipped with a movable conveyer belt, but the above explained polymerization methods are no more than examples, and the present invention is not limited thereto.

For example, hydrogel polymer may be obtained by supplying hot air into a reactor equipped with a stirring axis such as a kneader or heating the reactor, thus progressing thermal polymerization, and the hydrogel polymer discharged to the outlet of the reactor may be in the form of a few centimeters to a few millimeters according to the shape of the stirring axis equipped in the reactor. Specifically, the size of obtained hydrogel polymer may vary according to the concentration of the introduced monomer composition and the introduction speed, etc., and commonly, hydrogel polymer having a particle size of 2 to 50 mm may be obtained.

And, in case photopolymerization is progressed in a reactor equipped with a movable conveyer belt as explained above, the obtained hydrogel polymer may be in the form of a sheet having the width of the belt. Here, the thickness of the polymer sheet may vary according to the concentration of the introduced monomer composition and the introduction speed, but, commonly, a monomer composition is preferably fed such that polymer in the form of a sheet having a thickness of about 0.5 cm to about 5 cm may be obtained. In case a monomer composition is fed such that the thickness of sheet-shaped polymer may be too thin, production efficiency may be low, and if the thickness of the sheet-shaped polymer is greater than 5 cm, due to the too thick thickness, a polymerization reaction may not uniformly occur throughout the whole thickness.

Meanwhile, the moisture content of the thermally polymerized or photopolymerized hydrogel polymer may be 40 to 80 wt %. Throughout the specification, the "moisture content" is the content of moisture occupied based on the total weight of hydrogel polymer, and it means a value obtained by subtracting the weight of polymer of a dry state from the weight of hydrogel polymer. Specifically, it is defined as a value calculated by measuring the weight loss according to moisture evaporation in the polymer while raising the temperature of polymer through infrared heating to dry. At this time, the drying condition is established such that the temperature is raised from room temperature to about 180° C. and then maintained at 180° C., and the total drying time is 20 minutes including a temperature raising step of 5 minutes.

Next, the obtained hydrogel polymer is dried. At this time, if necessary, in order to increase the efficiency of the drying step, a step of coarse grinding may be conducted before drying.

Here, grinders that can be used in the coarse grinding is not limited in terms of the constructions, but specifically, one selected from the group consisting of a vertical pulverizer, a turbo cutter, a turbo grinder, a rotary cutter mill, a cutter mill, a disc mill, a shred crusher, a crusher, a chopper, a disc cutter may be used, but is not limited thereto.

The coarse grinding step may be progressed such that the particle diameter of hydrogel polymer may become about 2 to about 10 mm.

Grinding to a particle diameter of less than 2 mm would not be technically easy due to the high moisture content of the hydrogel polymer, and may generate agglomeration between the ground particles. Meanwhile, if grinding to a particle diameter greater than 10 mm, the effect of increasing the efficiency of the subsequent drying step may be insignificant.

The hydrogel polymer ground as explained above, or hydrogel polymer immediately after polymerization is passed through a drying step, and the drying temperature may be about 150° C. to about 250° C. Throughout the specification, "drying temperature" may be defined as the temperature of heating medium supplied for drying or the temperature of a drying reactor including heating medium and polymer in the drying process.

If the drying temperature is less than about 150° C., a drying time may too lengthen, and the properties of the finally prepared superabsorbent polymer may be deteriorated, and if the drying temperature is greater than about 250° C., only the surface of hydrogel polymer may be dried, thus generating a lot of fine particles in the grinding process as described below, and the properties of the finally prepared superabsorbent polymer may be deteriorated. Preferably, the drying may be progressed at a temperature of about 150 to about 200° C., more preferably at about 160 to about 180° C.

Meanwhile, the drying may be progressed for about 20 minutes to about 90 minutes considering the process efficiency, etc., but the drying time is not limited thereto.

And, the drying method is not limited in terms of the construction as long as it can be commonly used as a drying process of hydrogel polymer. Specifically, in the drying step, hot wind supply, infrared ray irradiation, ultrahigh frequency wave irradiation, or UV irradiation, etc., may be applied. The polymer dried by such a method may exhibit a moisture content of about 0.1 to about 10 wt %.

Next, a step of grinding the dried polymer obtained through the drying step is progressed.

The weight average particle diameter of the polymer powder obtained after the final grinding step may be about 150 μm to about 850 μm. As a grinder for grinding to such a particle diameter, specifically, a pin mill, a hammer mill, a screw mill, a roll mill, a disc mill, or a jog mill, etc. may be used, but the grinder is not limited thereto.

And, in order to manage the properties of the finally productized superabsorbent polymer after the grinding step, a step of sieving the polymer powder obtained after grinding according to the particle diameter may be conducted. Preferably, polymer with a particle diameter of about 150 μm to about 850 μm may be sieved, and only the polymer powder having such particle diameters may be additionally passed through the step of surface cross linking reaction.

Next, a surface crosslinking agent is added to the ground polymer to progress a surface crosslinking reaction.

The surface crosslinking is a step of increasing the crosslinking density near the polymer particle surface compared to the crosslinking density inside of the particle. In general, the surface crosslinking agent is coated on the surface of polymer particles. Thus, this reaction occurs on the surface of polymer particle, which improves crosslinkability on the particle surface without substantially influencing the inside of the particle. Thus, the surface crosslinked polymer particles have higher crosslinking degree near the surface compared to the inside.

In the preparation method of superabsorbent polymer of the present invention, a surface crosslinking reaction is conducted using a surface crosslinking agent comprising hydrophobic alcohol.

According to one embodiment of the present invention, the hydrophobic alcohol may be one or more selected from the group consisting of polyhydric alcohols having a carbon number of 4 or more. More specifically, it may be polyhydric alcohol having a carbon number of 4 to 10, preferably 4 to 7, and comprising a branched alkyl group, and preferably, 2,2-dimethyl-1,3-propanediol may be used.

Although using alcohols as surface crosslinking agent is known, hydrophilic alcohol, for example, alcohol having a carbon number of 3 or less such as 1,3-propandiol (1,3-PDO) was used previously. However, in case such hydrophilic alcohol is used as a surface crosslinking agent, as the reaction time increases, the penetration degree of the surface cross linking agent becomes too deep, and thus, there is a tendency that crosslinking progresses even to the inside of polymer. If a crosslinking reaction progresses even inside of polymer, the crosslinking density increases, and thus, centrifuge retention capacity (CRC) and absorbency under load (AUL) decreases, thus causing deterioration of the properties of the final product. Meanwhile, in order to prevent this, the surface crosslinking reaction time may be reduced or the reaction temperature may be lowered, but in this case, there is a concern that surface crosslinking may not sufficiently occur. Namely, it was difficult to control the penetration depth of the surface crosslinking agent.

Meanwhile, in the preparation method of superabsorbent polymer of the present invention, by using hydrophobic alcohol as a surface crosslinking agent, the above problem was solved. In case hydrophobic alcohol is added to polymer to progress a surface crosslinking reaction, due to the hydrophobic property, penetration into the polymer is difficult, and thus, the crosslinking reaction occurs only on the surface. Thus, even if a crosslinking reaction time increases, crosslinking inside the polymer hardly occurs, but a crosslinking region is formed only on the polymer surface, and centrifuge retention capacity and absorbency under load of base resin may be maintained.

The hydrophobic alcohol may be used in the content of about 0.01 to about 10 parts by weight, preferably about 0.01 to about 5 parts by weight, more preferably about 0.01 to about 1 part by weight, based on 100 parts by weight of the polymer.

If the content of the hydrophobic alcohol is too small, a surface crosslinking reaction may hardly occur, and if it is too large, due to the progression of excessive surface crosslinking reaction, deterioration of absorption capacity and properties may be generated.

According to one embodiment of the present invention, silica or clay may be further included as a surface crosslinking agent. Since the silica or clay are porous, the penetration of superabsorbent polymer can be further improved as they are added as surface crosslinking agents.

The method of adding the surface crosslinking agent to polymer is not limited in terms of the construction. The surface crosslinking agent and polymer powder may be put in a reactor and mixed, or the surface crosslinking agent may be sprayed to the polymer powder surface, or the surface crosslinking agent and polymer may be continuously supplied to a continuously operated mixer and mixed.

When adding the surface crosslinking agent, water, lower alcohol (for example, methanol) or a mixture thereof may be mixed and added as a solvent. If the solvent is added, there is an advantage in that the surface crosslinking agent may be uniformly dispersed on the polymer. Here, it is preferable that the solvent may be added in the content of about 0.1 to about 1 part by weight, based on 100 parts by weight of the polymer, so as to induce uniform dispersion of the surface crosslinking agent, prevent the agglomeration of polymer powder, and optimize the penetration depth of the crosslinking agent.

By heating the polymer particles to which the surface crosslinking agent is added at a temperature of about 140 to about 220° C., preferably about 160 to about 200° C. for about 15 to about 120 minutes, preferably about 30 to about 110 minutes, surface crosslinking and drying may be simultaneously achieved. If the crosslinking reaction temperature is less than 140° C., a surface crosslinking reaction may not occur, and it if is greater than 220° C., due to carbonization, foreign substance and odor may be generated, or due to excessive reaction, properties may be deteriorated and stable operation conditions may not be secured. And, if the crosslinking reaction time is less than 20 minutes, sufficient crosslinking reaction may not occur, and if it is greater than 120 minutes, due to excessive surface crosslinking, polymer particles may be damaged and the properties may be deteriorated.

A means to increase temperature for surface crosslinking is not specifically limited. A heating medium may be supplied, or a heat source may be directly supplied to heat. Here, the kind of heating medium that can be used may include steam, hot air, temperature-risen fluid such as hot oil, etc., but the present invention is not limited thereto, and the temperature of supplied heating medium may be appropriately selected considering the means of heating medium, temperature rise speed and target temperature to be raised. Meanwhile, as the directly supplied heat source, electric heating, gas heating, etc. may be mentioned, but the present invention is not limited thereto.

The superabsorbent polymer obtained according to the above preparation method of the present invention has improved centrifuge retention capacity, absorbency under load and penetration.

The superabsorbent polymer prepared according to the preparation method of the present invention has centrifuge retention capacity (CRC) measured according to EDANA method WSP 241.2 of about 25 g/g to 50 g/g, preferably about 30 g/g to about 40 g/g, and absorbency under pressure (AUP) measured according to EDANA method WSP 242.2 of about 10 g/g to about 30 g/g, preferably about 15 g/g to about 30 g/g, thus exhibiting excellent centrifuge retention capacity and absorbency under load. Particularly, in the case of absorbency under load, compared to the case wherein hydrophobic alcohol is not used as a surface crosslinking agent, about 5% or more, for example, about 5 to 20%, or about 10 to about 20% improvement effect in absorbency under load may be exhibited.

Hereinafter, the actions and effects of the invention will be explained in more detail through specific examples. However, these examples are presented only as the illustrations of the invention, and the scope of the invention is not determined thereby.

EXAMPLE

Preparation Example: Preparation of Base Resin 100 g of acrylic acid, 121.5 g of 32% caustic soda (NaOH), 0.2 g of sodium persulfate as a thermal polymerization initiator, 0.008 g of diphenyl(2,4,6-trimethylbenzoyl)phosphine oxide as a photopolymerization initiator, 0.23 g of polyethyleneglycol diacrylate (PEGDA, product name: Mirama 280, available from Miwon Chemical, weight average molecular weight: 400 g/mol) and 36.6 g of water were mixed to prepare a monomer composition having an acrylic acid concentration of 46 wt %.

The monomer composition was fed on a rotary belt having a width of 10 cm and a length of 2 m and rotating at a speed of 50 cm/min, at a feed speed of 500 to 2,000 mL/min. Simultaneously with feeding of the monomer composition, UV was irradiated at the intensity of 10 mW/cm² to progress a polymerization reaction for 60 seconds. After the polymerization reaction is completed, the product was cut by meat chopper and dried at 180° C. for 1 hour using a convection oven.

After drying, the dried material was ground with a grinder and sieved to select those of 150 to 850 μm size, thus preparing based resin with centrifuge retention capacity of 50 g/g.

Example 1

100 g of the base resin of Preparation Example (centrifuge retention capacity (CRC) 50 g/g, absorbency under load (AUL) 7.8 g/g) was mixed with 3.2 g of water, 4.0 g of methanol, 0.088 g of 2,2-dimethyl-1,3-propandiol and 0.008 g of silica (product name DM30S) to conduct a surface crosslinking reaction at 185° C. for 60 minutes.

After the surface crosslinking reaction, sieving with an ASTM standard sieve gave superabsorbent polymer having a particle size of 150 μm to 850 μm.

Example 2

Superabsorbent polymer was prepared by the same method as Example 1, except conducting a surface crosslinking reaction for 80 minutes.

Example 3

Superabsorbent polymer was prepared by the same method as Example 1, except conducting a surface crosslinking reaction for 110 minutes.

Comparative Example 1

100 g of the base resin of Preparation Example was mixed with 3.2 g of water, 4.0 g of methanol, 0.088 g of 1,3-propandiol and 0.008 g of silica (product name DM30S) were mixed to conduct a surface crosslinking reaction at 185° C. for 50 minutes.

After the surface crosslinking reaction, sieving with an ASTM standard sieve gave superabsorbent polymer having a particle size of 150 μm to 850 μm.

Comparative Example 2

Superabsorbent polymer was prepared by the same method as Comparative Example 1, except conducting a surface crosslinking reaction for 60 minutes.

Comparative Example 3

Superabsorbent polymer was prepared by the same method as Comparative Example 1, except conducting a surface crosslinking reaction for 90 minutes.

EXPERIMENTAL EXAMPLE

For the superabsorbent polymers prepared in Examples and Comparative Examples, the properties were measured by the following methods, and the results are shown in Table 1.

1) Centrifuge Retention Capacity (CRC)

For the superabsorbent polymers of Examples and Comparative Examples, centrifuge retention capacity (CRC) by the absorption scale under no load was measured according to EDANA method WSP 241.2.

Specifically, the polymer obtained in Examples and Comparative Examples was sieved into 300~600 μm size, and W (g, about 0.2 g) of the polymer was uniformly put in an envelope made of non-woven fabric and sealed, and then, immersed in a 0.9 wt % saline solution at room temperature. After 30 minutes, the envelope was drained at 250 G for 3 minutes using a centrifuge, and then, the mass W2 (g) of the envelope was measured. And, after the same operation without using polymer, the mass W1 (g) at that time was measured. Using the obtained masses, CRC (g/g) was calculated according to the following Formula.

$$CRC\ (g/g) = \{(W2\ (g) - W1\ (g) - W\ (g))\}/W\ (g))$$ [Formula 1]

In the Formula,

W (g) is the initial weight of superabsorbent polymer (g),

W1 (g) the weight of non-woven envelope in which superabsorbent polymer is not put, measured after immersed in a 0.9 wt % saline solution at room temperature for 30 minutes, and then, drained using a centrifuge at 250 G for 3 minutes, W2 (g) is the weight of non-woven envelope in which superabsorbent polymer is put, measured after immersed in a 0.9 wt % saline solution at room temperature for 30 minutes, and then, drained using a centrifuge at 250 G for 3 minutes.

2) Absorbency Under Load (AUL)

For the superabsorbent polymers of Examples and Comparative Examples, absorbency under load was measured according to EDANA method WSP 242.2.

Specifically, the obtained polymer was sieved into 300~600 μm size, W (g) (about 0.16 g, A) of the polymer was uniformly distributed on the AUL cylinder, and then, a weight of 0.9 psi was put thereon and the weight was measured (B). It was put on a Petri dish containing 0.9 mass % of a saline solution, and swollen for 60 minutes. After 60 minutes, it was taken out and the weigh was measured (C).

Using the obtained masses, AUL (g/g) was calculated according to the following Formula.

$$AUL\ (g/g) = (C-B)/A$$ [Formula 2]

In the Formula,

A is the weight of absorbent polymer (g),

B is the weight of the AUL Kit assembly after putting absorbent polymer,

C is the weight of the AUL Kit assembly after swelling for 60 minutes in a 0.9 wt % saline solution.

TABLE 1

|  | CRC(g/g) | AUL (g/g) |
| --- | --- | --- |
| Example 1 | 34.9 | 25.9 |
| Example 2 | 33.7 | 26.1 |
| Example 3 | 30.5 | 26.3 |
| Comparative Example 1 | 35.2 | 25.9 |
| Comparative Example 2 | 33.8 | 24.6 |
| Comparative Example 3 | 30.9 | 23.4 |

As can be seen from the Table 1, Examples using hydrophobic alcohol as a surface crosslinking agent exhibited improved absorbency under load ranges compared to Comparative Examples using hydrophilic alcohol under the same reaction conditions.

And, in Comparative Examples 1 to 3, both centrifuge retention capacity and absorbency under load decreased as a surface crosslinking reaction time increased, while in Examples 1 to 3, centrifuge retention capacity slightly decreased, but absorbency under load was maintained without decrease.

What is claimed is:

1. A method for preparing a superabsorbent polymer, comprising:
    thermal polymerizing or photopolymerizing a monomer composition comprising water-soluble ethylenically unsaturated monomers and a polymerization initiator to form a hydrogel polymer;
    drying the hydrogel polymer;
    grinding the dried polymer; and
    surface crosslinking the ground polymer in the presence of a surface crosslinking agent consisting of a polyhydric alcohol and porous silica or clay to form the superabsorbent polymer, wherein the polyhydric alcohol having a carbon number of 4 to 5 and having a branched alkyl group.

2. The method according to claim 1, wherein the polyhydric alcohol is 2,2-dimethyl-1,3-propanediol.

3. The method according to claim 1, wherein the polyhydric alcohol is included in the content of 0.01 to 10 parts by weight, based on 100 parts by weight of the polymer.

4. The method according to claim 1, wherein the centrifuge retention capacity (CRC) of the superabsorbent polymer is 25 g/g to 50 g/g, and the absorbency under pressure (AUP) is 10 g/g to 30 g/g.

5. The method according to claim 1, wherein the surface crosslinking step is conducted at a temperature of 140 to 220° C. for 15 to 120 minutes.

6. The method according to claim 5, wherein the centrifuge retention capacity (CRC) of the superabsorbent polymer is 35 g/g to 50 g/g, and the absorbency under pressure (AUP) is 25 g/g to 30 g/g.

7. The method according to claim 1, wherein the surface crosslinking step is conducted at a temperature of 185 to 200° C. for 60 to 110 minutes.

8. The method according to claim 7, wherein the centrifuge retention capacity (CRC) of the superabsorbent polymer is 30 g/g to 35 g/g, and the absorbency under pressure (AUP) is 25 g/g to 27 g/g.

9. The method according to claim 8, wherein the polyhydric alcohol is 2,2-dimethyl-1,3-propanediol.

10. The method according to claim 1, wherein the particle size of the super absorbent polymer ranges from 150 μm to 850 μm.

11. The method according to claim 1, wherein the water-soluble ethylenically unsaturated monomers include one or more selected from the group consisting of anionic monomers, non-ionic hydrophilic group containing monomers, and amino group containing unsaturated monomers.

12. The method of claim 11, wherein the anionic monomers are selected from the group consisting of acrylic acid, methacrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid, 2-(meth)acrylamide-2-methyl propane sulfonic acid, and salts thereof.

13. The method of claim 11, wherein the non-ionic hydrophilic group containing monomers are selected from the group consisting of (meth)acrylamide, N-substituted (meth)acrylate, 2-hydroxyethyl (meth)acrylate, 2-hydroxypropyl (meth)acrylate, methoxy polyethylene glycol (meth)acrylate, and polyethylene glycol (meth)acrylate.

14. The method of claim 11, wherein the amino group containing unsaturated monomers are selected from the group consisting of (N,N)-dimethylaminoethyl (meth)acrylate, (N,N)-dimethylaminopropyl (meth)acrylamide, and quaternarized products thereof.

* * * * *

UNITED STATES PATENT AND TRADEMARK OFFICE
CERTIFICATE OF CORRECTION

| | |
|---|---|
| PATENT NO. | : 11,198,768 B2 |
| APPLICATION NO. | : 15/755325 |
| DATED | : December 14, 2021 |
| INVENTOR(S) | : Ju Eun Kim et al. |

It is certified that error appears in the above-identified patent and that said Letters Patent is hereby corrected as shown below:

On the Title Page

Insert the following:
-- (30) Foreign Application Priority Data
December 23, 2015 (KR).............10-2015-0184917 --

Page 1 of 1

Signed and Sealed this
Tenth Day of May, 2022

Katherine Kelly Vidal
*Director of the United States Patent and Trademark Office*